Figure 1:
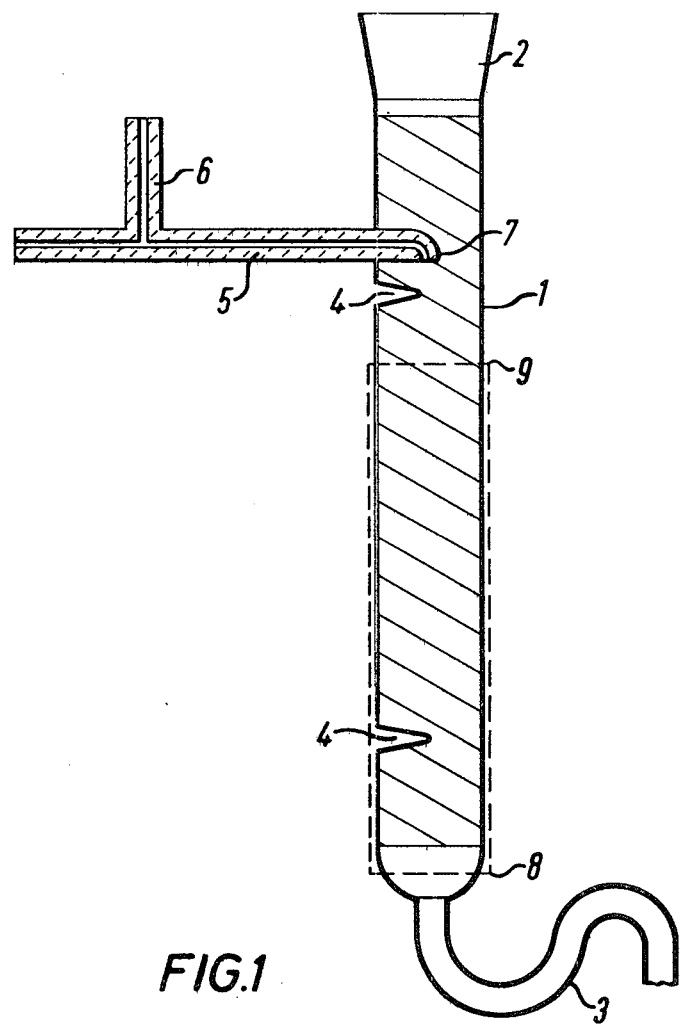

United States Patent [19]

Wirth

[11] 4,246,203
[45] Jan. 20, 1981

[54] PROCESS FOR THE PRODUCTION OF A PHENOL AND A CARBONYL COMPOUND BY THE CATALYZED DECOMPOSITION OF AN AROMATIC HYDROPEROXIDE

[75] Inventor: Max M. Wirth, Culross, Scotland

[73] Assignee: BP Chemicals Limited, London, England

[21] Appl. No.: 65,074

[22] Filed: Aug. 9, 1979

[30] Foreign Application Priority Data

Aug. 18, 1978 [GB] United Kingdom ............ 33857/78

[51] Int. Cl.³ ...................... C07C 37/08; C07C 45/53
[52] U.S. Cl. .................................. 568/385; 568/741;
568/768; 568/798; 568/815; 568/485; 568/342
[58] Field of Search ....................... 260/593 A, 580 R;
568/798, 741, 768, 815

[56] References Cited

U.S. PATENT DOCUMENTS

| | | | |
|---|---|---|---|
| 2,986,583 | 5/1961 | Rabbers et al. ................. | 260/593 A |
| 2,993,074 | 7/1961 | Shepard .............................. | 568/768 |
| 3,271,457 | 9/1966 | Bewley et al. .................... | 260/593 A |
| 3,497,561 | 2/1970 | Gelbein .............................. | 568/798 |
| 3,672,961 | 6/1972 | Nixon ................................ | 260/593 A |

*Primary Examiner*—James H. Reamer
*Attorney, Agent, or Firm*—Brooks, Haidt, Haffner & Delahunty

[57] ABSTRACT

The invention relates to a process in which an aromatic hydroperoxide of formula:

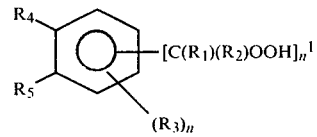

wherein independently $R_1$ is methyl or ethyl, $R_2$ is hydrogen, methyl or ethyl, or where $R_1$ and $R_2$ together form an alicyclic ring of 5 or 6 carbon atoms, $R_3$ is hydrogen or alkyl and $R_4$ and $R_5$ are hydrogen, alkyl or together form an automatic ring, n is 0, 1 or 2 and $n^1$ is 1 or 2, is converted to a phenol and a carbonyl compound in a catalyzed cleavage decomposition reaction. In particular cumene hydroperoxide is converted to phenol and acetone. Instead of removing the decomposition products from the reactor in the liquid phase and dissipating the reaction heat as in prior art processes the heat is used to remove the phenol and the carbonyl compound in the vapor phase leaving a liquid residue of higher-boiling compounds and catalyst in the case where a liquid cleavage catalyst is employed. Although a wide range of both solid and liquid cleavage catalysts may be used sulphuric acid is preferred. Various additives, including the hydrocarbon from which the hydroperoxide is derived and polar reaction products may be added. Typical reaction conditions are temperatures in the range 120° to 200° C. and either atmospheric or sub-atmospheric pressure. The process of the invention avoids the conventional catalyst neutralization and removal steps.

19 Claims, 2 Drawing Figures

PROCESS FOR THE PRODUCTION OF A PHENOL AND A CARBONYL COMPOUND BY THE CATALYZED DECOMPOSITION OF AN AROMATIC HYDROPEROXIDE

The present invention relates to a process for producing phenols and carbonyl compounds by cleaving an aromatic hydroperoxide in the presence of a catalyst. In particular the invention relates to the production of phenol and acetone by the catalytic cleavage decomposition of cumene hydroperoxide.

The production of phenol by the oxidation of isopropyl benzene, otherwise known as cumene, to cumene hydroperoxide, which is thereafter subjected to a cleavage reaction, generally in the presence of an acid catalyst, to produce a liquid cleavage reaction product containing as principal products phenol and acetone is well known. The liquid cleavage reaction product, which may also contain cumene and α-methylstyrene, after removal of any catalyst, is subjected to a series of purification steps in which phenol and acetone are recovered. The cleavage reaction product also contains various other products which are condensation products of phenol with eg α-methylstyrene, and it is necessary for the efficient operation of the process to recover the phenol from such condensation products in a cracking operation for recycle to the purification steps. Alpha-methylstyrene also recovered in the purification steps is normally hydrogenated to form cumene which is recycled to the oxidation stage.

In such processes the cleavage reaction is conventionally carried out in the presence of a low boiling solvent such as acetone itself, the heat of reaction being removed by refluxing the acetone. The cumene hydroperoxide feed to the cleavage reaction is usually a concentrate obtained by a two stage concentration step in which the cumene oxidation product is converted from about 22% hydroperoxide concentration to about 80% concentration. The recovered unreacted cumene is recycled to the oxidation stage. In a normal cleavage reaction carried out at about 80° C. the total make of acetone will be refluxed seven times to remove the heat of reaction with ensuing waste of low grade heat, consumption of cooling water and refrigerant and loss of acetone in vents.

An improved method of carrying out the cleavage decomposition of aromatic hydroperoxides has now been found.

Accordingly the present invention is a process in which a hydroperoxide of an aromatic compound of formula:

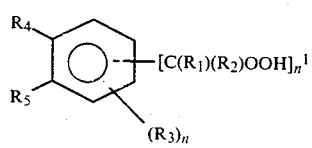

wherein independently $R_1$ is methyl or ethyl, $R_2$ is hydrogen, methyl or ethyl, or where $R_1$ and $R_2$ together form an alicyclic ring of 5 or 6 carbon atoms, $R_3$ is hydrogen or alkyl and $R_4$ and $R_5$ are hydrogen, alkyl or together form an aromatic ring, n is 0, 1 or 2 and $n^1$ is 1 or 2, is converted to a phenol and a carbonyl compound in a cleavage decomposition reaction which process comprises continuously feeding the hydroperoxide to a reactor in which it is contacted with a cleavage decomposition catalyst at an elevated temperature and at a pressure such that cleavage decomposition of the hydroperoxide occurs, the reactor being capable of separating the vapourised relatively low-boiling components from higher-boiling liquid products and catalyst, and continuously removing from the reactor a mixture in the vapour phase containing the phenol and the carbonyl compound cleavage decomposition products and in the liquid phase higher-boiling residues.

One embodiment of the invention provides for continuously feeding a liquid cleavage decomposition catalyst to the reactor and removing continuously from the reactor the catalyst in the liquid phase with the higher-boiling residues.

An alternative embodiment of the invention provides for continuously feeding the hydroperoxide of formula (I) to the reactor containing a fixed bed of a solid cleavage decomposition catalyst and removing the higher-boiling residues in the liquid phase continuously from the reactor.

An example of a suitable hydroperoxide having the formula (I) in which $R_4$ and $R_5$ together form an aromatic ring is isopropylnaphthyl hydroperoxide.

Preferably the hydroperoxide has the formula:

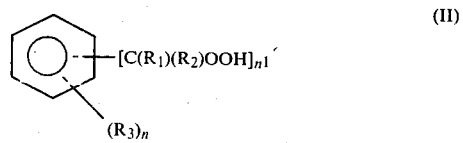

wherein independently $R_1$ is methyl or ethyl, $R_2$ is hydrogen, methyl or ethyl or where $R_1$ and $R_2$ together form an alicyclic ring of 5 or 6 carbon atoms, and wherein $R_3$ is hydrogen or alkyl, n is 0, 1 or 2 and $n^1$ is 1 or 2.

Examples of suitable hydroperoxides having the formula (II) are cumene-, cymene, cyclohexylbenzene-, diisopropylbenzene-, ethylbenzene- and sec-butylbenzene-hydroperoxides. Preferably the hydroperoxide is cumene hydroperoxide which is converted in the process of the present invention to phenol and acetone.

Hydroperoxides having the formulae (I) and (II) may be prepared in known manner by oxidation of the corresponding aromatic compound.

It is preferred to feed the hydroperoxide together with a diluent which may suitably be the aromatic hydrocarbon from which the hydroperoxide is derived. Alternatively, or additionally, other inert hydrocarbons, such as toluene, may be added as diluent.

It is further preferred to add a reaction modifier. Conveniently the reaction modifier may be one or more polar hydroperoxide cleavage decomposition products. Suitably the concentration of the reaction modifier may be in the range 5 to 55% w/w.

The hydroperoxide concentration is preferably such that the heat evolved during cleavage decomposition is the amount required to remove from the reactor at the cleavage decomposition temperature and pressure a mixture in the vapour phase containing the phenol and the carbonyl compound and in the liquid phase higher-boiling residues, without providing additional heat or removing surplus heat.

The cleavage decomposition catalyst is preferably an acid catalyst. Such catalysts may conveniently be divided into liquid phase catalysts and solid catalysts.

Whilst organic acids such as carboxylic acids may be used as the liquid phase cleavage decomposition catalyst it is preferred to employ a mineral acid catalyst, such as sulphuric acid or phosphoric acid, of which sulphuric acid is preferred. The liquid catalyst may be recovered from the liquid phase removed from the reactor and re-cycled to the reactor. Suitable solid catalysts which may be used include silica/alumina and polymers containing acidic functional groups, eg—$SO_3H$. Other cleavage decomposition catalysts which may be used include certain sulphur compounds, eg sulphur dioxide and sulphur itself, Lewis acids etc.

The elevated temperature may suitably be in the range from 120° to 200° C., preferably about 150° C. for atmospheric pressure operation. Whilst operation at atmospheric pressure is preferred it may be desirable on occasion to operate at sub-atmospheric pressure. It is also possible to operate at super-atmospheric pressure.

The process of the present invention may be carried out in any suitable reactor which provides for rapid removal of the mixture containing the phenol and carbonyl compound cleavage decomposition products in the vapour phase and also for the removal of a liquid phase, which usually takes the form of a tar. A suitable form of reactor is a boiler provided with heating means for the purpose of initiating the cleavage decomposition reaction. Since the residue usually takes the form of a highly viscous tar it may be advantageous to use as the reactor a short column provided with a reboiler.

The phenol and the carbonyl compound contained in the mixture removed in the vapour phase from the reactor may be recovered and purified in conventional manner.

Since of all the phenols, phenol itself is produced on the commercial scale in the largest tonnages the remainder of the description will be devoted to the cleavage decomposition of cumene hydroperoxide to produce phenol and acetone. It is well within the skill of the man in the art to optimise the conditions for the cleavage decomposition of other hydroperoxides.

In the case of cumene hydroperoxide cleavage decomposition the mixture removed in the vapour phase from the reactor preferably has a boiling point at standard temperature and pressure of less than 200° C. and contains phenol and acetone.

Cumene hydroperoxide may be prepared, for example, by feeding a mixture of purified cumene and purified recycle cumene to an oxidation vessel together with a dilute soda ash solution, in order to maintain the pH between 6.0 and 8.0. This mixture may be contacted with air and held at 110° to 115° C. until 20 to 25% is converted to the hydroperoxide. Many variations of this method are known and may be employed to produce a cumene hydroperoxide feedstock for use in the process of the present invention. It is preferred to use as feed a commercially available cumene hydroperoxide stream which may contain associated impurities such as phenyldimethyl carbinol and acetophenone. Alternatively the cumene hydroperoxide may be purified to remove such impurities.

Preferably the cumene hydroperoxide is diluted with cumene. Preferably acetone is added to the cumene hydroperoxide as a reaction modifier.

The preferred feedstock is a solution of cumene hydroperoxide at a concentration in the range 40 to 50% by weight, the solvent being one or more of the aforesaid impurities, diluents or reaction modifiers, because at concentrations in this range the heat of reaction is sufficient to vapourise, at the prevailing decomposition temperature, substantially all of the reaction products having a boiling-point of less than 200° C. including phenol and acetone. If the concentration of cumene hydroperoxide in the starting material is higher than about 50% by weight the decomposition will generate more heat than is needed to vapourise at atmospheric pressure the reaction products having a boiling-point of less than 200° C., and in this case some provision for cooling is required, for instance by generating steam. Alternatively the pressure at which the decomposition is carried out could be increased. In the event that the feedstock has a concentration of cumene hydroperoxide of less than about 40% by weight the decomposition reaction will not generate sufficient heat to vapourise the reaction products having a boiling point of less than 200° C. and in this case it would be necessary to provide additional heat.

Preferably the catalyst is sulphuric acid, which is suitably fed to the cleavage decomposition reaction as a dilute solution in, for example, one or more of acetone or acetophenone or cumene in an amount of from 50 to 2000 ppm of free acid, based on the weight of the feed.

Under these conditions it is believed that the formation of high-boiling condensation products of phenol is minimised. In any event, using an acid catalyst, many of these condensation products, once formed, are decomposed in the liquid phase, thus eliminating the need for a subsequent cracking operation. A further advantage of the present invention is that the heat of reaction is recoverable as sensible and latent heat in the product vapour fed to the product recovery and purification stages and, when a relatively involatile liquid phase catalyst such as sulphuric acid is used, the catalyst is removed from the product in the liquid phase with the small amount of high-boiling residues formed, thus eliminating the need for a separate catalyst removal stage.

It is preferred to use as the reactor a short column provided with a reboiler. Crude acetophenone recycled from the downstream purification stages may be fed a few plates up the column, but below the cumene hydroperoxide feed point. By refluxing this at 204° C. the necessary heat to initiate the reaction may be obtained, whereafter the heat input to the reboiler is reduced and the acetophenone will wash down and dilute the tar. Compounds boiling above 200° C. at standard temperature and pressure which may be found in the tar include acetophenone, cumyl phenols and alpha-methylstyrene dimers. At the same time the phenol content of the acetophenone recycle stream is recovered overhead as a vapour with the main phenol product. Naturally the reactor must be constructed of materials substantially resistant to the acid catalyst used, and the presence of trace heavy metal salts is preferably avoided as they will catalyse the undesirable decomposition of cumene hydroperoxide to phenyl dimethyl carbinol and acetophenone.

The process of the present invention provides a number of advantages including lower capital costs of the plant by eliminating catalyst removal, cracking and its associated distillation equipment needed in the conventional plants operated with liquid phase removal of product from the cleavage reactor. The process of the present invention also has a lower operating cost particularly arising from the feeding of vapour rather than liquid to the distillation system. The process also provides an inherent safety factor by eliminating the risk of accumulation of cumene hydroperoxide in the cleavage reactor due to failure of the catalyst supply. In the process of the present invention failure of the catalyst supply will merely lead to a thermal degradation reaction taking over with no risk of accumulation of cumene hydroperoxide to dangerous levels.

The process of the invention is illustrated by the following Examples.

In Examples 4 to 10 and 14 to 20 the glass reactor illustrated in FIG. 1 was employed. With reference to FIG. 1 the reactor consists of a 16 cm×2 cm glass tube (1) having at its upper end a B19/26 socket (2) through which vapourised reaction product is removed and at its lower end a smaller diameter tube (3) through which liquid residue is removed. Thermocouple pockets (4) are provided in the tube. A glass capillary tube (5) having a branch (6) serves to introduce the hydroperoxide feed and the catalyst feed respectively into the glass tube (1). The capillary tube is bent at its end (7) within the tube in order to direct the reactants downwards. That portion of the exterior of the tube between points (8) and (9) is covered by an electrical heating jacket, the remainder of the tube being lagged to prevent heat loss.

In Examples 1 to 3 and 11 to 13 a reactor identical to that illustrated in FIG. 1 except that the capillary tube (5) did not have a branch (6) was used.

Figure 2:
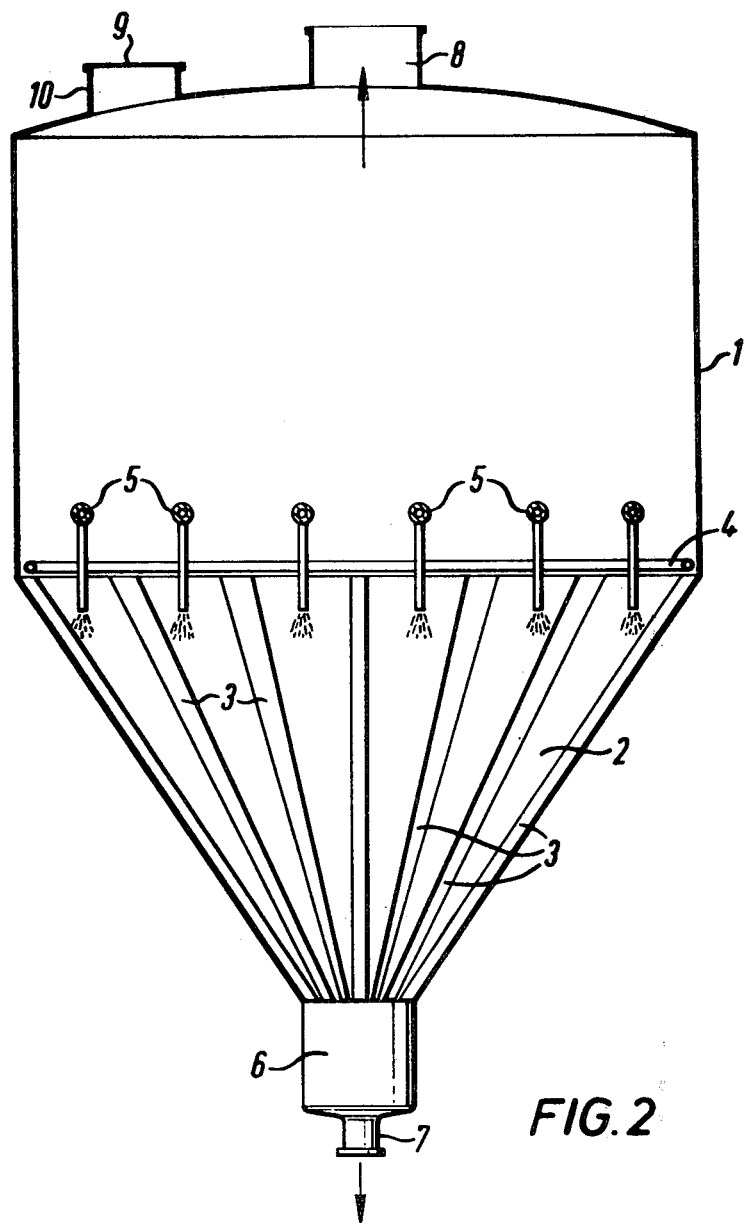

In Example 21 the stainless steel reactor illustrated in FIG. 2 was used. Its overall dimensions are a diameter of approximately 7 cm and a height of 40 cm. Referring to FIG. 2 the reactor consists of two sections, an upper cylindrical section (1) and a lower conical section (2). The conical section (2) has internal 'fins' (3) welded to the body to increase the internal surface area. Mounted above the 'fins' are two sparger rings (4) and (5) for introduction of the hydroperoxide and catalyst feed streams. The conical section (2) tapers into a chamber (6) for collection of the residue which is pumped out through the outlet (7). Vapourised product is removed through the outlet (8) and a bursting disc (9) is fitted to the outlet 10. The exterior of the upper cylindrical section (1) is lagged and steam traced and the lower conical section (2) is steam heated.

EXAMPLE 1

A 53% w/w solution of cumene hydroperoxide in cumene, containing 180 ppm of sulphuric acid was pumped at 50 ml/h into the top of a short ceramic packed reactor similar to that shown in FIG. 1. The bottom section, up to within 5 cm of the feed point, was heat compensated to maintain a skin temperature of 200° C. Cleavage occurred as soon as the feed touched the hot packing and products distilled overhead at a temperature of 152° C. The distillate accounted for 93% of the weight fed and the residual tar and acid drained from the bottom accounted for 3% of the weight fed. The distillate contained 22.8 mole % of phenol and 18.6 mole % of acetone.

EXAMPLE 2

A 48.3% w/w solution of cumene hydroperoxide in cumene containing 270 ppm of sulphuric acid was pumped at 100 ml/h into the top of a reactor similar to that shown in FIG. 1. The bottom section, up to within 5 cm of the feed point, was heat compensated to maintain a skin temperature of 200° C. A small section of stainless steel gauze was inserted below the feed point but above the heated section to act as a reaction zone and a similar small section of stainless steel gauze was inserted above the bottom and within the heated section to act as a cracking zone. Cleavage occurred as soon as the feed touched the hot packing and products distilled overhead at a temperature of 155° C. The distillate accounted for 96% of the weight fed and contained 21.6 mole % of phenol, 15.7 mole % of acetone and 10.9 mole % α-methylstyrene. A tar containing acid was drained from the bottom of the reactor.

EXAMPLE 3

A cumene solution containing 44.8% w/w of cumene hydroperoxide, 0.91% w/w acetophenone, 2.65% w/w dimethylphenyl carbinol and 285 ppm bw sulphuric acid was fed at 200 ml/h to the reactor similar to that illustrated in FIG. 1 containing a shallow layer (2 cm) of Monel gauze in an otherwise empty tube. The actual reaction zone thus consisted only of the Monel gauze.

The products distilled at 153° C. and the distillate amounted to 97% of the weight fed. The yield of phenol was 80 mole %, that of acetone 83 mole % and the main by-product was alpha-methyl styrene.

The 3% of residue consisted of a tar (at room temperature) and contained all the acid catalyst fed.

EXAMPLES 4 to 8

In these Examples the reactor illustrated in FIG. 1 containing a shallow layer (2 cm) of Monel gauze was used. A 0.5% w/w solution of sulphuric acid in acetone was fed as a separate stream through a common inlet with the cumene hydroperoxide. The concentration of sulphuric acid in the total feed was maintained at 230–390 ppm but the total feed rate was varied from 50 to 530 ml/h. The feed contained 48.5% w/w cumene hydroperoxide, 2.9% w/w phenyldimethyl carbinol and 0.7% w/w acetophenone.

The molar yield of phenol in the vapourised products is given in the following Table. The molar yield of acetone, which was also formed, is not given. A tar containing acid was drained from the bottom of the reactor.

TABLE

| Example | Feedrate (ml/h) | Phenol yield (mole %) |
|---------|-----------------|----------------------|
| 4 | 50 | 65 |
| 5 | 100 | 71 |
| 6 | 200 | 78 |
| 7 | 400 | 79 |
| 8 | 530 | 79 |

The above results demonstrate that optimally sufficient vapour velocity should be maintained in the reaction zone to remove the products as fast as they are formed.

OPERATION AT REDUCED PRESSURE

EXAMPLE 9

A cumene solution containing 40.2% w/w cumene hydroperoxide, 0.65% w/w acetophenone and 2.44% w/w phenyldimethyl carbinol was fed at 400 ml/h to the reactor illustrated in FIG. 1 packed with 3 mm stainless steel gauze rings, the reactor being maintained at a pressure of 500 mm absolute. A solution of 1.0% w/w sulphuric acid in acetophenone was fed as a separate stream through a common inlet with the cumene solution at such a rate that the sulphuric acid concentration in the total feed was 365 ppm.

The products distilled at 140° C. and the distillate accounted for 96.7% of the total weight fed. The phenol and acetone yields were 86.4 mole % and 90.7 mole % respectively and the yield of alpha-methylstyrene was 3.8 mole %. A tar containing acid was drained from the bottom of the reactor.

EXAMPLE 10

The procedure of Example 9 was repeated using the same reactor and feed composition but the reactor was maintained at 300 mm pressure absolute and the acid concentration in the total feed was 310 ppm.

The products distilled at 130° C. and the distillate accounted for 99.7% of the total weight fed. The phenol and acetone yields were 91.6 mole % and 94.8 mole % respectively and the yield of alpha-methylstyrene was 2.9 mole %. A small amount of tar containing acid was removed from the bottom of the reactor.

USE OF CATALYSTS OTHER THAN SULPHURIC ACID

EXAMPLE 11

Acetic Acid

Apart from using 650 ppm of acetic acid in place of sulphuric acid as catalyst the procedure, reactor and feed composition were identical to Example 3.

The product distilled at 167° C. and gas was evolved at 30 ml/min (NPT). The yield of phenol was 31 mole %, that of acetone 40 mole %, that of acetophenone 33 mole % and that of alpha-methylstyrene 29 mole %. A tar containing acid was removed from the bottom of the reactor.

These results demonstrate that acetic acid is not a preferred catalyst in the process of the invention.

EXAMPLE 12

Sulphur Dioxide

Apart from using 100 ppm $SO_2$ in place of sulphuric acid as catalyst the procedure, reactor and feed composition were identical to Example 3. The $SO_2$ was pumped into the reactor as an acetone solution through a common feed line with the cumene hydroperoxide.

The products distilled at 146° C. and the distillate amounted to 92% of the weight fed. The phenol yield was 62 mole %. A tar was removed from the bottom of the reactor.

EXAMPLE 13

Sulphur

Apart from using 100 ppm sulphur in place of sulphur dioxide the procedure, reactor and feed composition were identical to Example 3. The sulphur was dissolved in boiling cumene and the resulting solution and suspension was fed to the reactor in the manner described in Example 12.

The yield of phenol was 60 mole %. A tar was removed from the bottom of the reactor.

EXAMPLE 14

Formic Acid

Apart from using 480 ppm of formic acid as catalyst in place of sulphuric acid and operating at atmospheric pressure the procedure, reactor and feed composition were identical to Example 9.

The products distilled at between 175° C. and 182° C. The following yields were obtained:

phenol: 13.1 mole %
acetone: 30.3 mole %
alpha-methylstyrene: 21.8 mole %
acetophenone: 48.8 mole %

A tar containing acid was removed from the bottom of the reactor.

EXAMPLE 15

Phosphoric Acid

Apart from using 475 ppm o-phosphoric acid as catalyst in place of formic acid the procedure, reactor and feed composition were identical to Example 9. The o-phosphoric acid was fed as a solution in acetone.

The product distilled at 146.5° C. and the distillate accounted for 97.3% of the total weight fed. The phenol and acetone yields were 77.6 mole % and 75.1 mole % respectively while the yield of alpha-methylstyrene was 11.2 mole %. A tar containing acid was removed from the bottom of the reactor.

EXAMPLE 16

Fluoroboric Acid

A cumene solution containing 39.9% w/w cumene hydroperoxide was fed at 400 ml/h to the reactor illustrated in FIG. 1 packed with 3 mm stainless steel gauze rings, operated at atmospheric pressure. A solution of fluoroboric acid in acetone was fed as a separate stream through a common inlet with the cumene/cumene hydroperoxide feed solution such that the acid concentration in the total feed was 395 ppm.

The products distilled at 163° C. and the distillate accounted for 96.2% of the total weight fed. The phenol and acetone yields were 25.4 mole % and 39.7 mole % respectively while the yields of alpha-methylstyrene and acetophenone were 6.4 mole % and 38.7 mole % respectively. A tar was removed from the bottom of the reactor.

EXAMPLE 17

Silica/alumina

A cumene solution containing 40.1% w/w cumene hydroperoxide, 0.65% w/w acetophenone and 2.43% w/w phenyldimethyl carbinol was fed at 200 ml/h to the reactor illustrated in FIG. 1 packed with silica/alumina pellets, the reactor being operated at atmospheric pressure.

Cleavage occurred on the silica/alumina and the products distilled at 148° C., the distillate accounting for 91.4% w/w of the total weight fed. The phenol and acetone yields were 56.7 mole % and 63.9 mole % respectively and the alpha-methylstyrene yield was 10.8 mole %. A tar was removed from the bottom of the reactor.

CLEAVAGE DECOMPOSITION OF HYDROPEROXIDES OTHER THAN CUMENE HYDROPEROXIDE

EXAMPLE 18

Ethylbenzene Hydroperoxide

An ethylbenzene solution containing 40.4% w/w ethylbenzene hydroperoxide was fed at 200 ml/h to the reactor illustrated in FIG. 1 packed with 3 mm stainless steel gauze rings. A solution of 0.5% sulphuric acid in acetophenone was fed as a separate stream through a common inlet with the ethylbenzene hydroperoxide at such a rate that the sulphuric acid concentration in the total feed was 175 ppm.

The product distilled at 150° C. and the distillate accounted for 91.6% of the total weight fed. The phenol yield was 70.5 mole % and that of acetaldehyde 54.5 mole %. A tar containing acid was removed from the bottom of the reactor.

EXAMPLE 19

Cyclohexylbenzene Hydroperoxide

A cyclohexylbenzene solution containing 39.95% w/w cyclohexylbenzene hydroperoxide was fed at 200 ml/h to a tubular reactor identical to that described in Example 9 but operated at atmospheric pressure. A solution of sulphuric acid in acetophenone was fed as a separate stream through a common inlet with the cyclohexylbenzene/cyclohexylbenzene hydroperoxide feed solution such that the acid concentration in the total feed was 245 ppm.

The products distilled at 233° C. and the distillate accounted for 90.7% w/w of the total weight fed. The phenol and cyclohexanone yields were 37.7 mole % and 40.6 mole % respectively. A tar containing acid was removed from the bottom of the reactor.

EXAMPLE 20

Use of Reaction Modifier

An acetone solution containing 40.5% w/w cumene hydroperoxide, 0.66% w/w acetophenone and 2.46% w/w phenyldimethyl carbinol was fed at 400 ml/h to the reactor illustrated in FIG. 1 packed with 3 mm stainless steel gauze rings. The reactor was operated at atmospheric pressure. A solution of 1.4% w/w sulphuric acid in acetone was fed as a separate stream through a common inlet with the acetone/cumene hydroperoxide solution at such a rate that the sulphuric acid concentration in the total feed was 300 ppm.

The products distilled at 136° C. and the distillate accounted for 96.2% of the total weight fed. The phenol and acetone yields were 91.7 mole % and 93.2 mole % respectively. A tar containing acid was removed from the bottom of the reactor.

EXAMPLE 21

Pilot Plant Operation

A cumene solution containing 39.7% w/w cumene hydroperoxide, 0.87% w/w acetophenone and 2.76% w/w phenyldimethyl carbinol was fed at 4 l/h through the lower sparger (5) in the reactor shown in FIG. 2, which was operated at atmospheric pressure with the conical section (2) temperature controlled at 193° C. A solution of 0.7% w/w sulphuric acid in acetophenone was fed through the upper sparger (4), so that the acid rained down on the incoming cumene hydroperoxide feed, at such a rate that the sulphuric acid concentration in the total feed was 650 ppm.

The products distilled at 155° C. and the distillate accounted for 91.5% of the total weight fed. The phenol and acetone yields were 67.8 mole % and 80.2 mole % respectively. A residue in the form of an acid tar was pumped from the chamber (6).

I claim:

1. A process in which a hydroperoxide of an aromatic compound of formula:

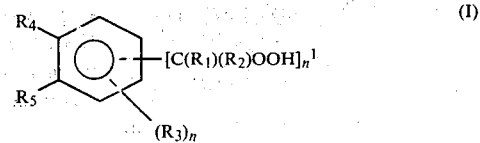

wherein independently $R_1$ is methyl or ethyl, $R_2$ hydrogen, methyl or ethyl, or where $R_1$ and $R_2$ together form an alicyclic ring of 5 or 6 carbon atoms, $R_3$ is hydrogen or alkyl and $R_4$ and $R_5$ are hydrogen, alkyl or together form an aromatic ring, n is 0, 1 or 2 and $n^1$ is 1 or 2, is converted to a volatile phenol and a carbonyl compound in a cleavage decomposition reaction which process comprises continuously feeding said hydroperoxide to a reactor in which it is contacted with a cleavage decomposition catalyst at an elevated temperature and at a pressure such that cleavage decomposition of the hydroperoxide occurs, said reactor being capable of separating the vapourised relatively low-boiling components from higher-boiling liquid products and catalyst and continuously removing from said reactor a mixture in the vapour phase containing said phenol and said carbonyl compound cleavage decomposition products and in the liquid phase higher-boiling residues.

2. A process according to claim 1 wherein a liquid cleavage decomposition catalyst is fed continuously to said reactor and is removed continuously from said reactor in said liquid phase with said higher-boiling residues.

3. A process according to claim 1 wherein said reactor contains a fixed bed of a solid cleavage decomposition catalyst.

4. A process according to claim 1 wherein said hydroperoxide has the formula:

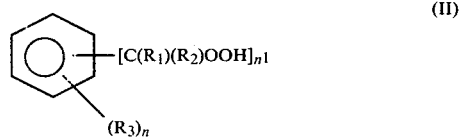

wherein independently $R_1$ is methyl or ethyl, $R_2$ is hydrogen, methyl or ethyl or where $R_1$ and $R_2$ together form an alicyclic ring of 5 or 6 carbon atoms and wherein $R_3$ is hydrogen or alkyl, n is 0, 1 or 2 and $n^1$ is 1 or 2.

5. A process according to claim 4 wherein said hydroperoxide of formula (II) is cumene-, cymene-, cyclohexylbenzene-, diisopropylbenzene-, ethylbenzene-, or sec-butylbenzene hydroperoxide.

6. A process according to claim 1 wherein said hydroperoxide is fed together with a diluent.

7. A process according to claim 6 wherein said diluent is the aromatic hydrocarbon from which said hydroperoxide is derived.

8. A process according to claim 1 wherein there is added a reaction modifier which is one or more polar hydroperoxide cleavage decomposition products.

9. A process according to claim 1 wherein said hydroperoxide concentration is such that the heat evolved during decomposition is the amount required to remove from said reactor at said cleavage decomposition temperature and pressure said mixture in said vapour phase containing said phenol and said carbonyl compound and in said liquid phase higher-boiling residues, without providing additional heat or removing surplus heat.

10. A process according to claim 1 wherein said cleavage decomposition catalyst is sulphuric acid.

11. A process according to claim 1 wherein said pressure is atmospheric or sub-atmospheric.

12. A process according to claim 1 wherein said reactor is a short column provided with a reboiler.

13. A process in which cumene hydroperoxide is converted to phenol and acetone in a cleavage decomposition reaction which process comprises continuously feeding said hydroperoxide to a reactor in which it is contacted with a cleavage decomposition catalyst at an elevated temperature and at a pressure such that cleavage decomposition of said hydroperoxide occurs, said reactor being capable of separating vapourised relatively low-boiling components from higher-boiling liquid products and catalyst, and continuously removing from said reactor a mixture in the vapour phase containing compounds having a boiling point at standard temperature and pressure of less than 200° C., including said phenol and said acetone, and in the liquid phase higher-boiling residues.

14. A process according to claim 13 wherein said cumene hydroperoxide feed to said reactor contains as impurities phenyldimethyl carbinol and/or acetophenone.

15. A process according to claim 13 wherein said cumene hydroperoxide feed contains cumene as diluent.

16. A process according to claim 13 wherein said cumene hydroperoxide feed contains acetone as a reaction modifier.

17. A process according to claim 13 wherein said cumene hydroperoxide is fed as a solution in a solvent selected from acetone, acetophenone cumene and mixtures thereof, the concentration of said cumene hydroperoxide being in the range 40 to 50% by weight.

18. A process according to claim 13 wherein said catalyst is sulphuric acid which is fed to said reactor as a dilute solution in a solvent selected from acetone, acetophenone, cumene and mixtures thereofin an amount of from 50 to 2000 ppm of free acid based on the weight of said feed and is removed from said reactor in the liquid phase with said higher-boiling residues.

19. A process according claim 13 said temperature is in the range 120° to 200° C. and said pressure is atmospheric.

* * * * *